(12) United States Patent
Sugai et al.

(10) Patent No.: US 6,395,439 B1
(45) Date of Patent: May 28, 2002

(54) NAPHTHOQUINONE DERIVATIVE AND ELECTROPHOTOSENSITIVE MATERIAL USING THE SAME

(75) Inventors: Fumio Sugai; Nobuko Akiba, both of Osaka (JP)

(73) Assignee: Kyocera Mita Corporation, Osaka (JP)

(*) Notice: Subject to any disclaimer, the term of this patent is extended or adjusted under 35 U.S.C. 154(b) by 0 days.

(21) Appl. No.: 09/594,038

(22) Filed: Jun. 15, 2000

(30) Foreign Application Priority Data

Jun. 30, 1999 (JP) .................................. 11-184611

(51) Int. Cl.$^7$ ...................... G03G 5/047; G03G 50/14
(52) U.S. Cl. ...................... 430/58.25; 430/56; 430/72; 430/83; 552/299
(58) Field of Search ...................... 552/299; 430/58.25, 430/56, 72, 83

(56) References Cited

U.S. PATENT DOCUMENTS 5,863,688 A * 1/1999 Watanabe et al. ............ 430/72

FOREIGN PATENT DOCUMENTS

| EP | 0 863 442 A2 | 9/1998 |
| JP | 1-206349 | 8/1989 |
| JP | 6-110227 | 4/1994 |
| JP | 9-151157 | 6/1997 |

OTHER PUBLICATIONS

HCAPLUS Abstract AN 1998:178658 of the article "Oxidation Reaction of 5–hydroxy–2,3–dihydrobenzofurans and 5–hydroxy–2,3–dihydronaphtho [1,2–b] furans," *Synthesis* (1998), (3), 293–296, 1998.*

* cited by examiner

*Primary Examiner*—Janis L. Dote
(74) *Attorney, Agent, or Firm*—Smith, Gambrell & Russell, LLP

(57) ABSTRACT

The present invention relates to a naphthoquinone derivative of the formula (1):

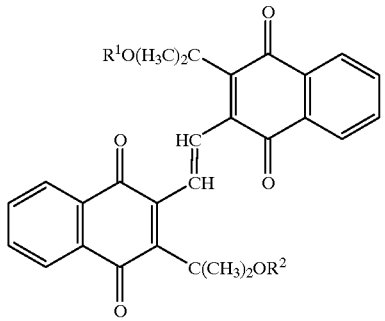

wherein $R^1$ and $R^2$ are the same or different and each represents a hydrogen atom or an alkyl group having 1 to 6 alkyl group, and the electrophotosensitive material comprises a conductive substrate and a photosensitive layer provided on the conductive substrate, wherein the photosensitive layer contains the naphthoquinone derivative (1).

7 Claims, 1 Drawing Sheet

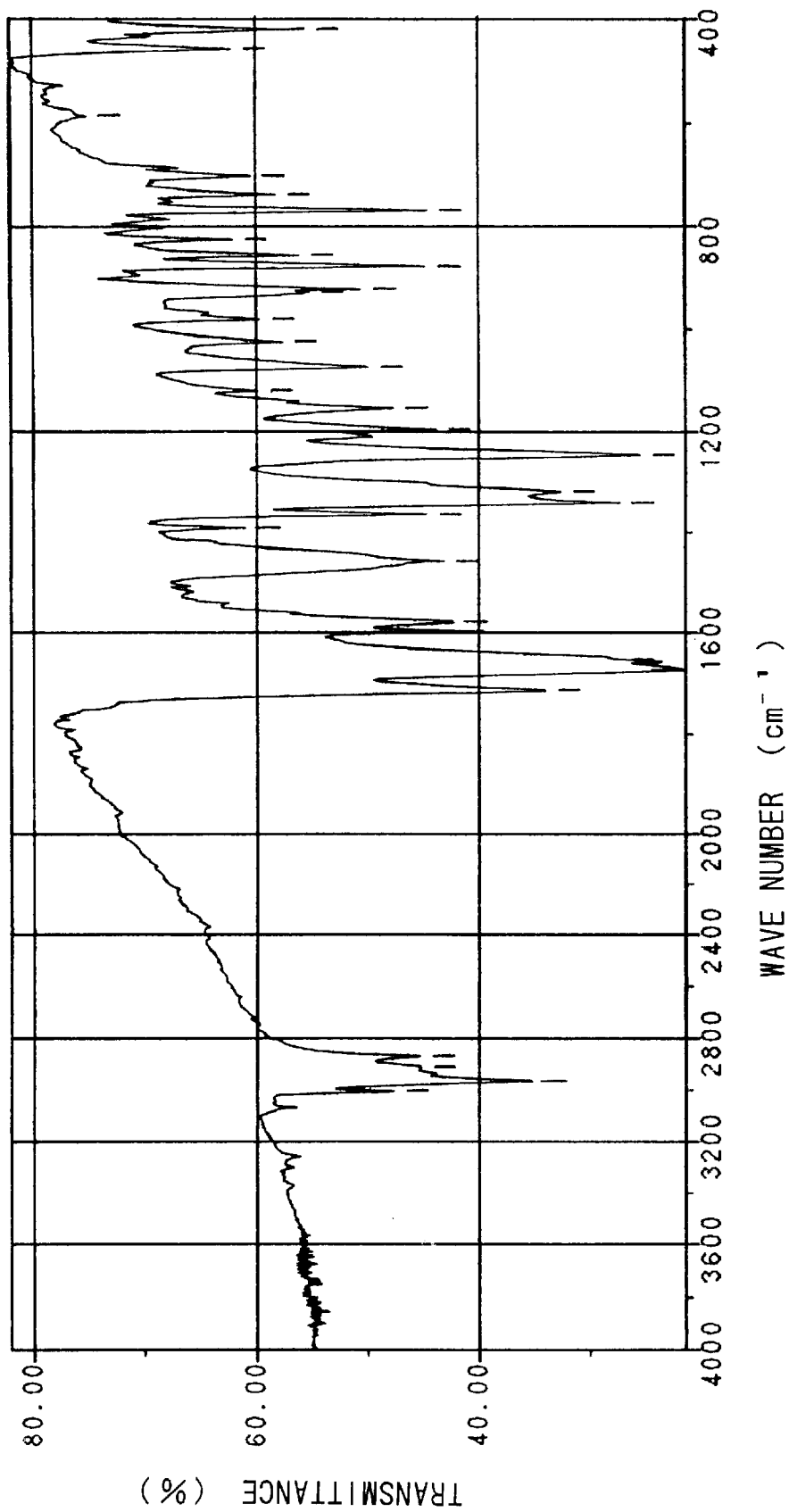

NAPHTHOQUINONE DERIVATIVE AND ELECTROPHOTOSENSITIVE MATERIAL USING THE SAME

BACKGROUND OF THE INVENTION

The present invention relates to a naphthoquinone derivative having excellent electric charge transferability, and an electrophotosensitive material containing the naphthoquinone derivative, which is used in image forming apparatuses such as antistatic copying machine, facsimile, laser beam printer and the like.

In the image forming apparatuses, so-called organic photosensitive materials comprising an electric charge generating material for generating electric charges by irradiation with light, an electric charge transferring material for transferring generated electric charges, and a binder resin constituting layer(s) in which these substances are dispersed have widely been used. In general, the organic photosensitive materials are classifies roughly into a photosensitive material having a single-layer type photosensitive layer wherein an electric charge generating material and an electric charge transferring material are contained in the same layer, and a photosensitive material having a multi-layer type photosensitive layer comprising an electric charge generating layer containing an electric charge generating material and an electron transferring layer containing an electron transferring material, which are mutually laminated. In the multi-layer type photosensitive layer, the electric charge transferring layer having a larger film thickness than that of the electric charge generating layer is generally provided on an outermost layer of the photosensitive material in view of the mechanical strength.

The electric charge transferring material used in these photosensitive materials includes those having hole transferability and those having electron transferability. Among electric charge transferring materials known at present, almost all of those having high carrier mobility, capable of imparting practical sensitivity to the photosensitive material, are those having hole transferability. Therefore, organic photosensitive materials, which are put into practice at present, are negative charging type photosensitive materials in case of the multi-layer type one wherein the electric charge transferring layer is provided on the outermost layer of the photosensitive material.

However, the negative charging type organic photosensitive material has problems such as influence of ozone on the environment and deterioration of the photosensitive material itself because it must be charged by negative corona discharge that causes evolution of a large amount of ozone.

To solve the above problems, it has been studied to use an electron transferring material as the electric charge transferring material. For example, Japanese Unexamined Patent Publication (Kokai) No. 1-206349 suggests that a compound having a diphenoquinone or benzoquinone structure is used as the electron transferring material.

However, since the compound having a diphenoquinone or benzoquinone structure generally has poor matching with the electric charge generating material, injection of electrons from the electric charge generating material into the electron transferring material is insufficient. Such an electron transferring material is not uniformly dispersed in a photosensitive layer because of its poor compatibility with a binder resin, so that a hopping distance of electrons becomes longer and electrons do not easily move in a low electric field.

Accordingly, a conventional photosensitive material containing an electron transferring material has a problem that the residual potential increases and the sensitivity becomes poor, as is apparent from electrical characteristics test described in the Examples described hereinafter.

The single-layer type photosensitive material has such an advantage that one photosensitive material can be used in any of positive charging type and negative charging type by using the electron transferring material in combination with the hole transferring material. However, when using a diphenoquinone derivative as the electron transferring material, there arises a problem that a charge transfer complex is formed by an interaction between the electron transferring material and hole transferring material, thereby to inhibit transfer of electrons and holes.

To improve the above problems, for example, Japanese Unexamined Patent Publication (Kokai) Nos. 6-110227 and 9-151157 suggest that a monomer of naphthoquinones is used as the electron transferring material.

However, the electric charge mobility is not sufficient in the monomer of the naphthoquinones. Therefore, the residual potential and photosensitivity were not satisfactory even when using this compound in the photosensitive material.

SUMMARY OF THE INVENTION

Thus, an object of the present invention is to solve the above technical problems, thereby to provide a novel compound suited for use as an electron transferring in an electrophotosensitive material.

Another object of the present invention is to provide an electrophotosensitive material whose sensitivity is improved as compared with the prior art.

The present inventors have intensively studied to attain the above objects and found a new fact that a naphthoquinine derivative represented by the general formula (1):

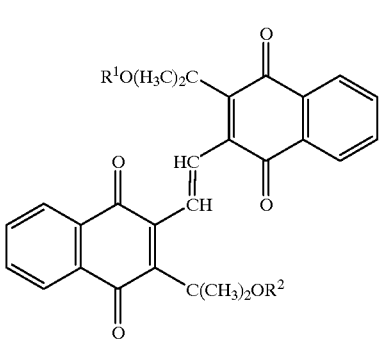

(1)

wherein $R^1$ and $R^2$ are the same or different and each represents a hydrogen atom or an alkyl group having 1 to 6 carbon atoms, has higher electron transferability than that of a conventional electron transferring material such as compound having a diphenoquinone structure or benzoquinone structure, and is superior in compatibility with a binder resin, thus completing the present invention.

Accordingly, the present invention relates to:

(i) A naphthoquinone derivative represented by the general formula (1).

(ii) An electrophotosensitive material comprising a conductive substrate and a photosensitive layer provided on the conductive substrate, wherein the photosensitive layer contains the naphthoquinone derivative represented by the general formula (1) of the item (i).

(iii) The electrophotosensitive material according to the item (ii), wherein an electron acceptor is contained in the photosensitive layer.

(iv) The electrophotosensitive material according to the item (ii), wherein the photosensitive layer is a single layer.
(v) The electrophotosensitive material according to the item (ii), wherein the photosensitive layer contains a phthalocyanine.
(vi) The electrophotosensitive material according to the item (ii), which is a positive charge type electrophotosensitive material.
(vii) The electrophotosensitive material according to the item (ii), which has an electric charge generating layer and an electric charge transferring layer on the upper side of the conductive substrate, wherein the electric charge generating layer is located inner side to the electric charge transferring layer.

Such a naphthoquinone derivative (1) is superior in electron acceptability, and is uniformly dispersed in a photosensitive layer because of its good compatibility with a binder resin. Injection of electrons from the electric charge material is smoothly conducted because of excellent matching with the electric charge material. Accordingly, the naphthoquinone derivative (1) exhibits excellent electron transferability even in a low electric field, and is suited for use as the electron transferring material in the electrophotosensitive material.

Furthermore, since the naphthoquinone derivative (1) does not form a charge transfer complex, together with the hole transferring material, it can be particularly suited for use in a single-layer photosensitive layer using the electron transferring material in combination with the hole transferring material.

The electrophotosensitive material of the present invention comprises a conductive substrate and a photosensitive layer provided on the conductive substrate, wherein the photosensitive layer contains the naphthoquinone derivative represented by the general formula (1).

Such an electrophotosensitive material has lower residual potential than that of a conventional electrophotosensitive material containing an electron transferring material and high sensitivity because a naphthoquinone derivative (1) having excellent characteristics described above is contained in a photosensitive layer.

That is, the photosensitive layer containing the naphthoquinone derivative (1) is superior in electron transferability in a low electric field and causes less rebinding of electrons and holes therein and, furthermore, an apparent electric charge generating rate approaches an actual value, thus improving the sensitivity of the photosensitive material having such a photosensitive layer. The residual potential of the photosensitive material is also lowered, thereby to improve the stability and durability on repeated exposure.

Since the naphthoquinone derivative (1) does not form the charge transfer complex, together with the hole transferring material as described above, a photosensitive material having higher sensitivity can be obtained when it is used in a single-layer type photosensitive material containing an electron transferring material and a hole transferring material in the same photosensitive layer.

The electron transferability is further improved when an electron acceptor is contained in the photosensitive layer, so that a photosensitive material having higher sensitivity can be obtained.

BRIEF DESCRIPTION OF THE DRAWING

FIG. 1 is a graph showing an infrared absorption spectrum of the naphthoquinone derivative corresponding to the compound (1-1) in Table 1.

MODE FOR CARRYING OUT THE INVENTION

First, the naphthoquinone derivative (1) of the present invention will be described in detail.

In the general formula (1), the alkyl group corresponding to the substituents $R^1$ and $R^2$ includes, for example, alkyl group having 1 to 6 carbon atoms, such as methyl, ethyl, n-propyl, isopropyl, n-butyl, isobutyl, s-butyl, t-butyl, n-pentyl, isopentyl, neopentyl, or n-hexyl. $R^1$ and $R^2$ may be the same or different.

As specific examples of the naphthoquinone derivative represented by the general formula (1), the substituents corresponding to $R^1$ and $R^2$ are shown in Table 1 below.

In Table 1, H denotes a hydrogen atom, Me denotes a methyl group, Et denotes an ethyl group, n-Pr denotes a n-propyl group, i-Pr denotes an isopropyl group, n-Bu denotes a n-butyl group, i-Bu denotes an isobutyl group, t-Bu denotes a t-butyl group, n-Pe denotes a n-pentyl group, and n-Hex denotes a n-hexyl group, respectively.

TABLE 1

| Number of compound | $R^1$ | $R^2$ |
|---|---|---|
| 1–1 | Me | Me |
| 1–2 | Me | H |
| 1–3 | Et | Et |
| 1–4 | Et | H |
| 1–5 | Me | Et |
| 1–6 | n-Pr | n-Pr |
| 1–7 | n-Pr | H |
| 1–8 | i-Pr | i-Pr |
| 1–9 | i-Pr | H |
| 1–10 | Me | i-Pr |
| 1–11 | Et | i-Pr |
| 1–12 | n-Pr | i-Pr |
| 1–13 | n-Bu | n-Bu |
| 1–14 | n-Bu | H |
| 1–15 | i-Bu | i-Bu |
| 1–16 | i-Bu | H |
| 1–17 | t-Bu | t-Bu |
| 1–18 | t-Bu | H |
| 1–19 | Me | t-Bu |
| 1–20 | H | H |
| 1–21 | n-Pe | n-Pe |
| 1–22 | n-Hex | n-Hex |

The method of synthesizing the naphthoquinone derivative (1) of the present invention will be described with reference to a naphthoquinone derivative corresponding to the compound number (1-1) in Table 1.

Reaction scheme (I)

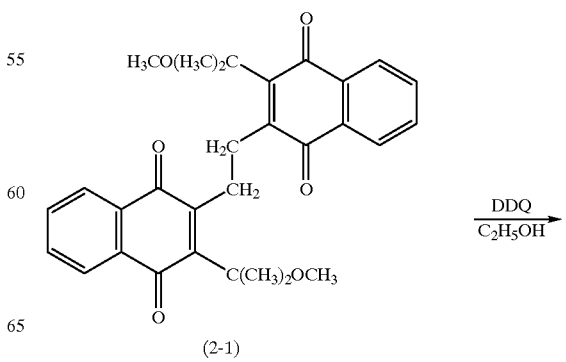

-continued

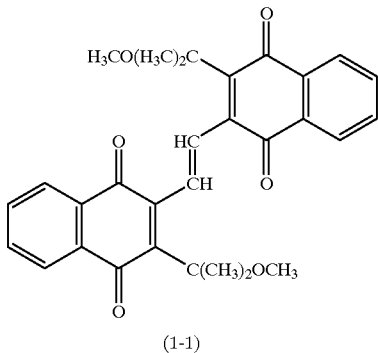

(1-1)

According to the reaction scheme (1), a naphthoquinone derivative (1-1) is obtained by dissolving a compound represented by the formula (2-1) in a solvent such as toluene, adding 2,3-dihydro-5,6-dicyclo-1,4-benzoquinone (DDQ), and reacting the mixture under reflux for 10 to 30 hours.

Reaction scheme (II)

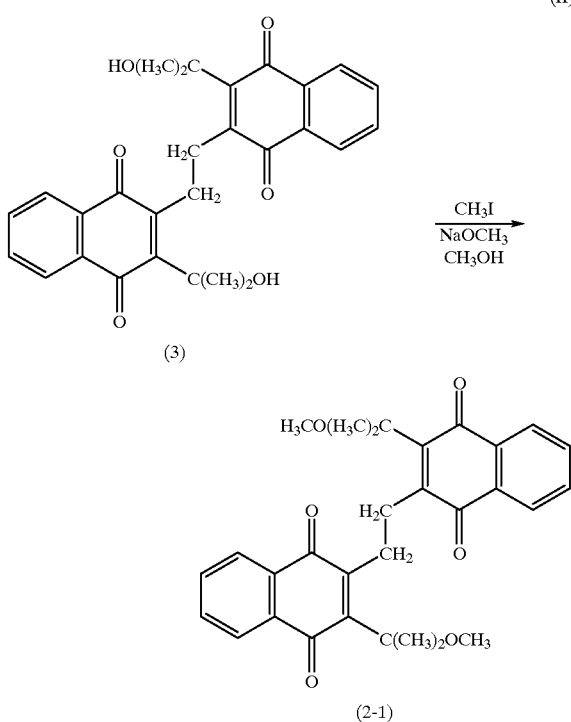

According to the reaction scheme (II), a compound represented by the formula (2-1) as a starting material of the reaction scheme (I) is obtained by dissolving a compound represented by the formula (3) in methanol, adding methyl iodide, further adding NaOCH$_3$, and reacting the mixture at room temperature for 1 to 5 hours. In this reaction, methyl iodide is used in an amount more than two times to molar quantity of the compound of the formula (3) to obtain the compound of the formula (2-1) which corresponds to the compound of the general formula (1) wherein R$^1$ and R$^2$ are the same (methyl groups).

Similarly, when other R$^1$I (or R$^2$I) and NaOR$^1$ (or NaOR$^2$) in replace of CH$^3$I and NaOCH$^3$ are used in the Reaction scheme (II), a compound having the corresponding alkyl groups in replace of the compound of the formula (2-1) can be synthesized.

Reaction scheme (III)

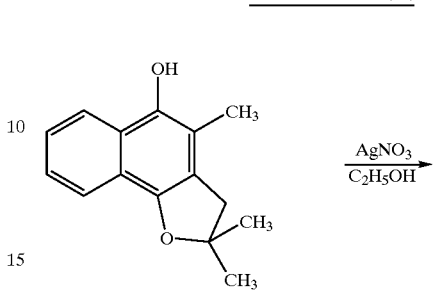

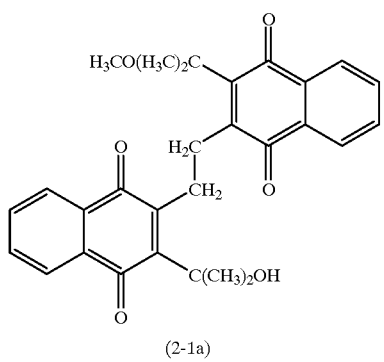

According to the reaction scheme (III), a compound represented by the formula (3) as a starting material of the reaction scheme (II) is obtained by adding a compound of the formula (4) (SYNTHESIS March 1998,293) and silver nitrate in ethanol, reacting the mixture with stirring, and refluxing the reaction solution for 10 to 60 minutes.

A naphthoquinone derivative represented by the general formula (1) wherein R$^1$ and R$^2$ are different can be synthesized for example as follows:

In Reaction scheme (II), methyl iodide is used in the amount of about equal molar quantity to that of the compound of the formula (3) to obtain the reaction mixture containing compounds of the formula (2-1a) and the formulas (2-1) together with unreacted compound of the formula (3).

(2-1a)

The compound of the formula (2-1a) is isolated from the reaction mixture by methods such as recrystallization, gas chromatography, and so forth. The compound of the formula (2-1a) is provided to obtain the compound of the formula (2-1b) according to Reaction scheme (IV).

Reaction scheme (IV)

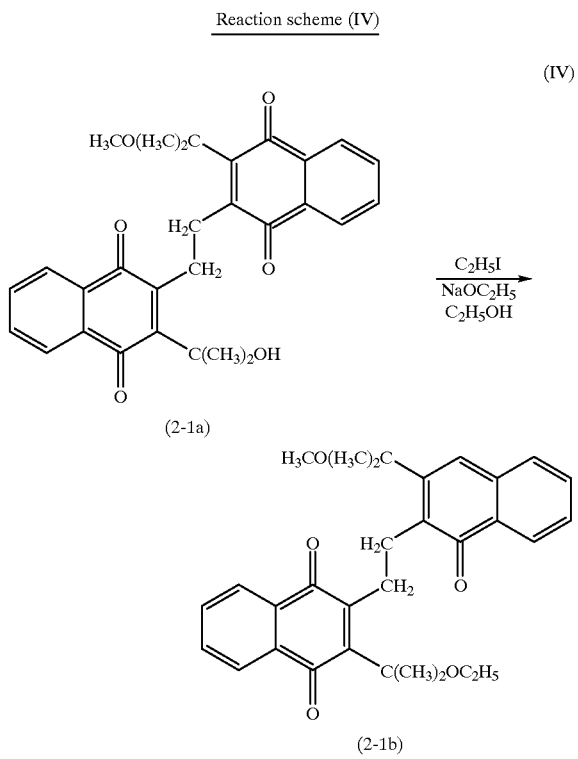

According to these methods, the naphthoquinone derivative (1) of the present invention can be efficiently obtained.

The electrophotosensitive material of the present invention will be described hereinafter.

The electrophotosensitive material of the present invention is that obtained by providing a photosensitive layer containing a naphthoquinone derivative represented by the general formula (1) on a conductive substrate.

The electrophotosensitive material of the present invention can be applied to any of a single-layer type photosensitive material and a multi-layer type photosensitive material, but the effect due to the use of the naphthoquinone derivative (1) of the present invention is markedly exerted in the single-layer type photosensitive material.

The single-layer type electrophotosensitive material is that obtained by providing a single photosensitive layer containing at least a naphthoquinone derivative (1) as an electron transferring material, an electric charge generating material and a binder resin on a conductive substrate. Such a single-layer type electrophotosensitive material can be applied to any of positive charging type and negative charging type with a single structure, but is preferably used in a positive charging type that requires no negative polarity corona discharge. This single-layer type photosensitive material had these advantages, for example, the productivity is excellent because of simple layer structure and film defects of the photosensitive layer are inhibited and, furthermore, optical characteristics can be improved because of less interface between the layers.

Regarding the single-layer type electrophotosensitive material using the naphthoquinone derivative (1) as the electron transferring material in combination with the hole transferring material having excellent hole transferability, an interaction between the nathphtoquinone derivative (1) and hole transferring material does not occur as described above. Therefore, even if both transferring materials are contained in the same photosensitive layer in high concentration, electrons and holes can be efficiently transferred to obtain an electrophotosensitive material having high sensitivity.

Regarding a single-layer type photosensitive material wherein an electron acceptor was contained, together with the naphthoquinone derivative (1), the electron transferability can be further improved to obtain a photosensitive material having high sensitivity.

On the other hand, the multi-layer electrophotosensitive material is obtained by providing an electric charge generating layer containing an electric charge generating material and an electric charge transferring layer containing an electric charge generating material on a conductive substrate in this order or a reverse order. Since the electric charge generating layer has a considerably smaller film thickness than that of the electric charge transferring layer, it is preferred that the electric charge generating layer is formed on the conductive substrate and the electric charge transferring layer is formed thereon in order to protect the electric charge generating layer.

The charging type (positive or negative) of the multi-layer type photosensitive material is selected according to the order of formation of the electric charge generating layer and electric charge transferring layer and the kind of the electric charge transferring material used in the electric charge transferring layer. With the layer structure where the electric charge generating layer is formed on the conductive substrate and the electric charge transferring layer is formed thereon, when using the electron transferring material such as naphthoquinone derivative (1) as the electric charge transferring material in the electric charge transferring layer, a positive charging type photosensitive material is obtained. In this case, the hole transferring material or electron transferring material may be contained in the electric charge generating layer. When the electron acceptor is contained in the electric charge transferring layer, the electron transferability is improved, thereby making it possible to obtain a multi-layer photosensitive material having higher sensitivity.

With the above layer structure, when using the hole transferring material as the electric charge generating material in the electric charge transferring layer, a negative charging type photosensitive material is obtained. In this case, the naphthoquinone derivative (1) or electron acceptor may be contained in the electric charge generating layer.

As described above, the electrophotosensitive material of the present invention can be applied to any of the single-layer type and multi-layer type. The single-layer type is preferred because of the following reasons. That is, the single-layer type can be used in both (negative and positive) charging types and can be easily produced because of its simple structure. Furthermore, film defects can be inhibited on formation of the film and the optical characteristics can be improved because of less interface between the layers.

Various materials used in the electrophotosensitive material of the present invention will be described below.

<Electric charge generating agent>

The electric charge generating material used in the present invention includes, for example, compounds represented by the following general formulas (CG1) to (CG-12).

(CG1) Metal-free phthalocyanine (CG 1)

(CG2) Oxotitanyl phthalocyanine (CG 2)

(CG3) Perylene pigment (CG 3)

wherein $R^{g1}$ and $R^{g1}$ are the same or different and each represents a substituted or non-substituted alkyl group having 18 or less carbon atoms, a cycloalkyl group, an aryl group, an alkanoyl group, or an aralkyl group (CG4) Bisazo pigment $$Cp^1-N{=}N-Q-N{=}N-Cp^2 \quad (CG\ 4)$$

wherein $Cp^1$ and $CP^2$ are the same or different and each represents a coupler residue; and Q represents each group represented by the following formulas:

(Q-1)

wherein $R^{g3}$ represents a hydrogen atom, an alkyl group, an aryl group or a heterocyclic group, with a proviso that an alkyl group, an aryl group or a heterocyclic group may have a substituent; and ω represents 0 or 1;

(Q-2)

(Q-3)

wherein $R^{g4}$ and $R^{g5}$ are the same or different and each represents a hydrogen atom, an alkyl group having 1 to 5 carbon atoms, a halogen atom, an alkoxy group, an aryl group, or an aralkyl group;

(Q-4)

or (Q-5)

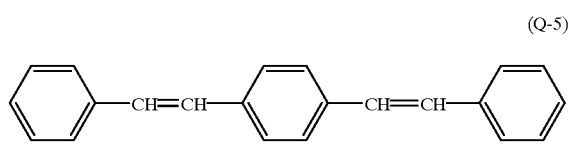

(Q-8)

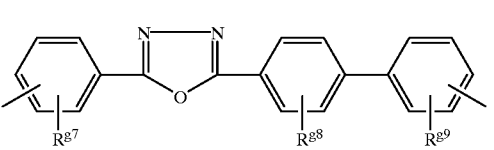

wherein $R^{g7}$, $R^{g8}$ and $R^{g9}$ are the same or different and each represents a hydrogen atom, an alkyl group having 1 to 5 carbon atoms, a halogen atom, an alkoxy group, an aryl group, or an aralkyl group (Q-6)

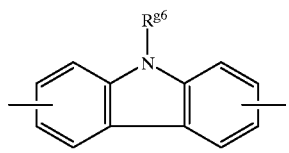

(CG5) Dithioketopyrrolopyrrole pigment (CG 5)

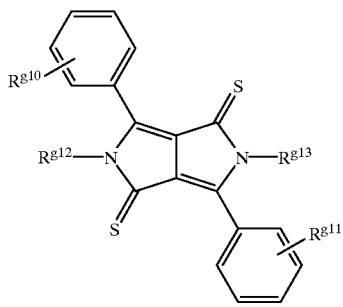

wherein $R^{g6}$ represents a hydrogen atom, an ethyl group, a chloroethyl group, or a hydroxyethyl group;

(Q-7)

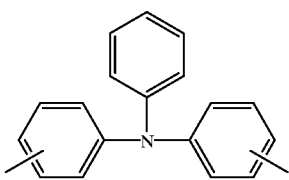

wherein $R^{g10}$ and $R^{g11}$ are the same or different and each represents a hydrogen atom, an alkyl group, an alkoxy group, or a halogen atom; and $R^{g12}$ and $R^{g13}$ are the same or different and each represents a hydrogen atom, an alkyl group, or an aryl group (CG6) Metal-free naphthalocyanine pigment (CG 6)

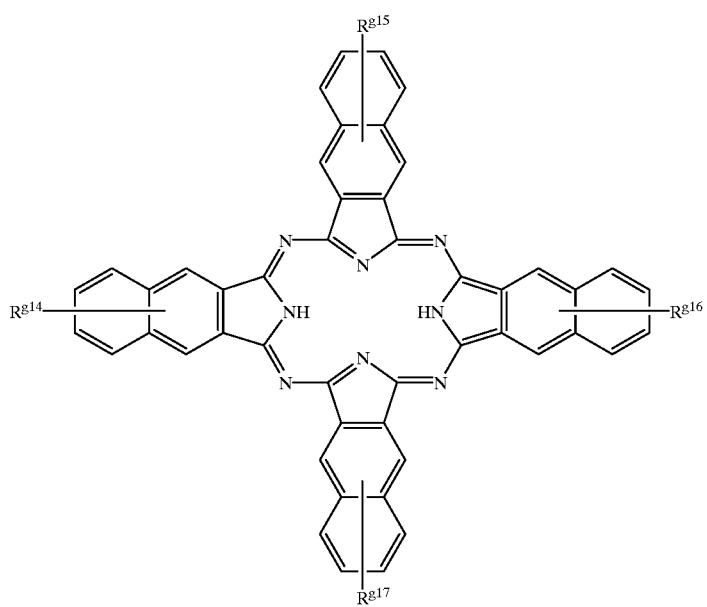

wherein $R^{g14}$, $R^{g15}$, $R^{g16}$ and $R^{g17}$ are the same or different and each represents a hydrogen atom, an alkyl group, an alkoxy group, or a halogen atom (CG7) Metallic phthalocyanine pigment

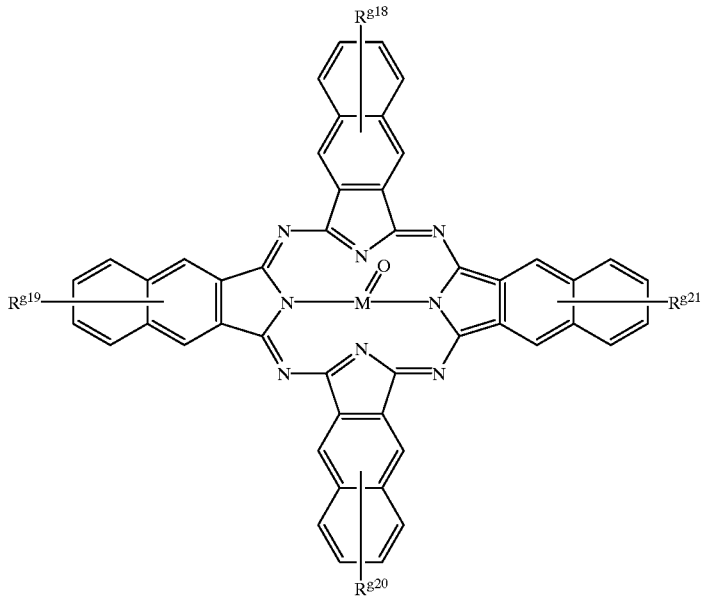

(CG 7)

wherein $R^{g18}$, $R^{g19}$, $R^{g20}$ and $R^{g21}$ are the same or different and each represents a hydrogen atom, an alkyl group, an alkoxy group, or a halogen atom; and M represents Ti or V (CG8) Squaline pigment

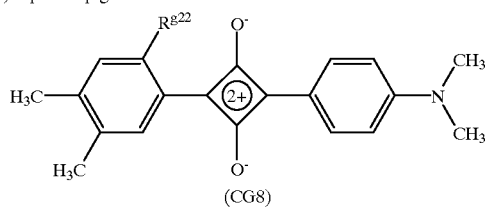

(CG8)

wherein $R^{g22}$ represents a hydrogen atom, an alkyl group, an alkoxy group, or a halogen atom (CG9) Trisazo pigment

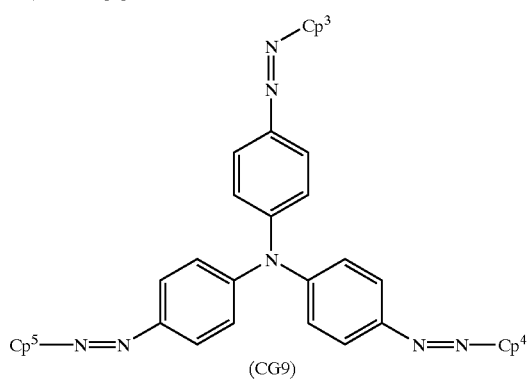

(CG9)

wherein $Cp^3$, $Cp^4$, and $Cp^5$ are the same or different and each represents a coupler residue (CG10) Indigo pigment

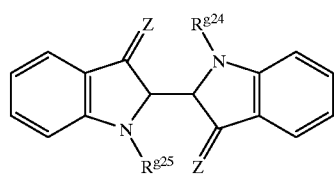

(CG 10)

wherein $R^{g24}$ and $R^{g25}$ are the same or different and each represents a hydrogen atom, an alkyl group, or an aryl group; and Z represents an oxygen atom or a sulfur atom (CG11) Azulenium pigment

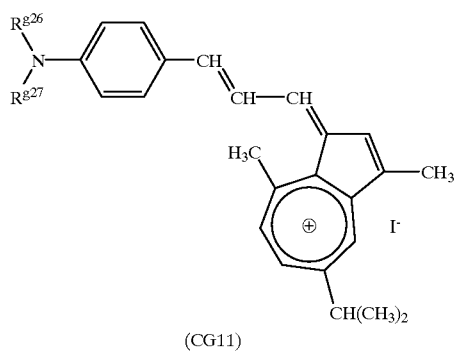

(CG11)

wherein $R^{g26}$ and $R^{g27}$ are the same or different and each represents a hydrogen atom, an alkyl group or an aryl group (CG12) Cyanine pigment

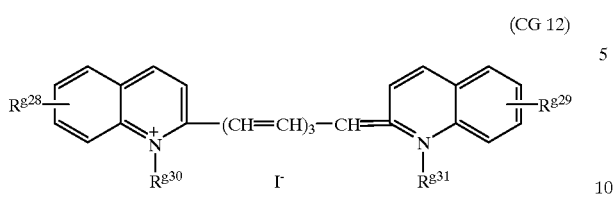
(CG 12)

wherein $R^{g28}$ and $R^{g29}$ are the same or different and each represents a hydrogen atom, an alkyl group, an alkoxy group, or a halogen atom; and $R^{g30}$ and $R^{g31}$ are the same or different and each represents a hydrogen atom, an alkyl group, or an aryl group.

In the electric charge generating materials described above, the alkyl group includes the same groups as those described above. The substituted or non-substituted alkyl groups having 18 or less carbon atoms are groups including heptyl, octyl, nonyl, decyl, dodecyl, tridecyl, pentadecyl and octadecyl, in addition to the alkyl group having 1 to 6 carbon atoms.

The cycloalkyl group includes, for example, groups having 3 to 8 carbon atoms, such as cyclopropyl, cyclobutyl, cyclopentyl, cyclohexyl, cycloheptyl, or cyclooctyl.

The alkoxy group and aryl group include the same groups as those described above. The alkanoyl group includes, for example, acetyl, formyl, propionyl, butynyl, pentanoyl, or hexanoyl. The halogen atom includes, for example, fluorine, chlorine, bromine, or iodine.

The heterocylic group includes, for example, ethynyl, furyl, pyrrolyl, pyrrolidinyl, oxazolyl, isoxazolyl, thiazolyl, isothiazolyl, imidazolyl, 2H-imidazolyl, piperidyl, piperidino, 3-morpholinyl, morpholino, or thiazolyl. It may also be a heterocyclic group condensed with an aromatic ring.

The substituted with which the above groups may be substituted includes, for example, halogen atom, amino group, hydroxyl group, optionally esterified carboxyl group, a cyano group, an alkyl group having 1 to 6 carbon atoms, an alkoxy group having 1 to 6 carbon atoms, or an alkenyl group having 2 to 6 carbon atoms which may have an aryl group.

The coupler residue represented by $Cp^1$, $Cp^2$, $Cp^3$, $Cp^4$ and $Cp^5$ includes, for example, groups represented by the following general formulas (Cp-1) to (Cp-11).

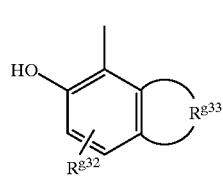
(Cp-1)

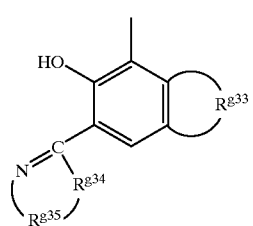
(Cp-2)

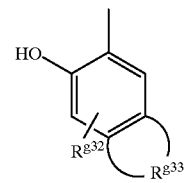
(Cp-3)

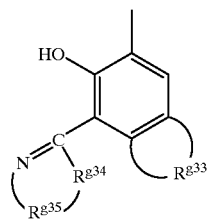
(Cp-4)

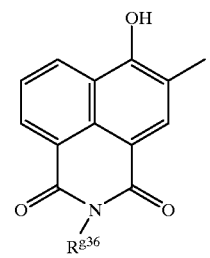
(Cp-5)

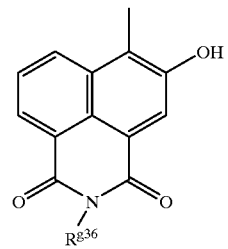
(Cp-6)

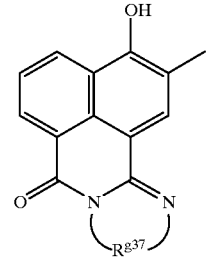
(Cp-7)

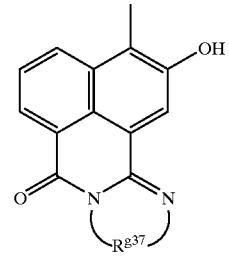
(Cp-8)

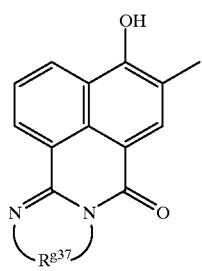
(Cp-9)

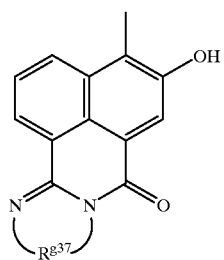
(Cp-10)

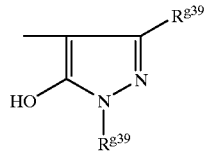
(Cp-11)

In the respective formulas, $R^{g32}$ represents a carbamoylgroup, asulfamoylgroup, anallophanoylgroup, an oxamoyl group, an anthraniloyl group, a carbazoyl group, a glycyl group, a hydantoyl group, a stalamoyl group, or a succinamoyl group. These groups may have a substituent such as halogen atom, optionally substituted phenyl group, optionally substituted naphthyl group, nitro group, cyano group, alkyl group, alkenyl group, carbonyl group, or carboxyl group.

$R^{g33}$ represents an atomic group required to form an aromatic ring, a polycyclic hydrocarbon or a heterocyclic ring by condensation with a benzene ring, and these rings may have the same substituents as those described above.

$R^{g34}$ represents an oxygen atom, a sulfur atom, or an imino group.

$R^{g35}$ represents a divalent chain hydrocarbon group or an aromatic hydrocarbon group, and these groups may have the same substituents as those described above.

$R^{g36}$ represents an alkyl group, an aralkyl group, an aryl group, or a heterocyclic group, and these groups may have the same substituents as those described above.

$R^{g37}$ represents an atomic group required to form a heterocyclic ring, together with a divalent chain hydrocarbon group or an aromatic hydrocarbon group, or together with two nitrogen atoms in the above substituents (Cp-1) to (Cp-11), and these groups may have the same substituents as those described above.

$R^{g39}$ represents an alkyl group or an aryl group, and these groups may have the same substituents as those described above.

The alkenyl group includes, for example, alkenyl group having 2 to 6 carbon atoms, such as vinyl, allyl, 2-butenyl, 3-butenyl, 1-methylallyl, 2-pentenyl, or 2-hexenyl.

The atomic group required to form an aromatic ring by condensation with a benzene ring in $R^{g33}$ includes, for example, alkylene group having 1 to 4 carbon atoms, such as methylene, ethylene, trimethylene, or tetramethylene.

The aromatic group to be formed by condensation of $R^{g33}$ with the benzene ring includes, for example, naphthalene ring, anthracene ring, phenanthrene ring, pyrene ring, chrysene ring, or naphthacene ring.

The atomic group required to form a polycyclic hydrocarbon by condensation with the benzene ring in $R^{g33}$ includes, for example, alkylene group having 1 to 4 carbon atoms, carbazole group, benzocarbazole group, or dibenzofuran ring.

The atomic group required to form a heterocyclic ring by condensation with the benzene ring in $R^{g33}$ includes, for example, benzofuranyl, benzothiophenyl, indolyl, 1H-indolyl, benzoxazolyl, benzothiazolyl, 1H-indadolyl, benzimidazolyl, chromenyl, chromanyl, isochromanyl, quinolinyl, isoquinolinyl, cinnolinyl, phtharazinyl, quinazolinyl, quinoxalinyl, dibenzofuranyl, carbazolyl, xanthenyl, acrydinyl, phenanthridinyl, phenazinyl, phenoxazinyl, or thianthrenyl.

The aromatic heterocyclic group to be formed by condensation of $R^{g33}$ with the benzene ring includes, for example, thienyl, furyl, pyrrolyl, oxazolyl, isoxazolyl, thiazolyl, isothiazolyl, imidazolyl, pyrrazolyl, triazolyl, tetrazolyl, or pyridyl. It may also be a heterocyclic group condensed with the other aromatic ring (e.g. benzofuranyl, benzoimidazole, benzoxazole, benzotriazole, quinolyl, etc.).

The divalent chain hydrocarbon group in $R^{g35}$ and $R^{g37}$ includes, for example, ethylene, trimethylene, or tetramethylene. The divalent aromatic hydrocarbon includes, for example, phenylene, naphthylene, or phenanthrene.

The heterocyclic group in $R^{g36}$ includes, for example, pyridyl, pyrazyl, thienyl, pyranyl, or indolyl.

The atomic group required to form a heterocyclic ring, together with two nitrogen atom, in $R^{g37}$ includes, for example, phenylene, naphthylene, phenanthrene, ethylene, trimethylene, or tetramethylene.

The aromatic heterocylic group to be formed by $R^{g37}$ and two nitrogen atoms includes, for example, benzimidazole, benz[f]benzimidazole, dibenzo[e,g]benzoimidazole, or benzopyrimidine. These groups may have the same substituents as those described above.

The alkoxycarbonyl group in $R^{g38}$ includes, for example, methoxycarbonyl, ethoxycarbonyl, propoxycarbonyl, or butoxycarbonyl.

In the present invention, there can be used powders of inorganic photoconductive materials, such as selenium, selenium-tellurium, selenium-arsenic, and cadmium sulfide, and amorphous silicon; and conventionally known electric charge generating materials such as pyrylium salt, anthanthrone pigment, triphenylmethane pigment, threne pigment, toluidine pigment, pyrazoline pigment, and quinacridone pigment.

Among these electric charge generating materials, for example, phthalocyanine pigments such as metal-free phthalocyanine represented by the general formula (CG1) and oxotitanyl phthalocyanine represented by the general formula (CG2) are preferably used because a photosensitive material having a sensitivity within a wavelength range of not less than 700 nm is required in image forming apparatuses such as laser beam printer using a light source such as semiconductor laser, and facsimile. The crystal form of the phthalocyanine pigment is not specifically limited, and various phthalocyanine pigments can be used.

For example, a perylene pigment represented by the general formula (CG3) and a bisazo pigment represented by the general formula (CG4) are preferably used in analogue optical image forming apparatuses such as antistatic copying machine using a white light source such as halogen lamp because a photosensitive material having a sensitivity within a visible range.

<Hole transferring material>

The hole transferring material used in the present invention includes various compounds having high hole transferability, for example, compounds represented by the general formulas (HT1) to (HT13).

(HT 1)

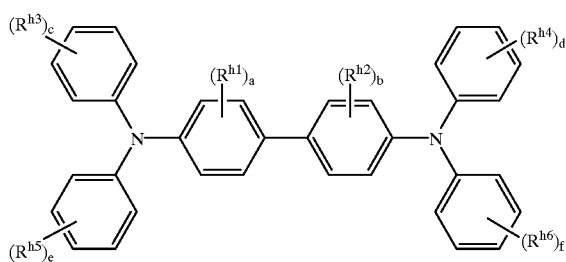

wherein $R^{h1}$, $R^{h2}$, $R^{h3}$, $R^{h4}$, $R^{h5}$ and $R^{h6}$ are the same or different and each represents a halogen atom, an alkyl group which may have a substituent, an alkoxy group which may have a substituent, or an aryl group which may have a substituent; a and b are the same or different and each represents an integer of 0 to 4; and c, d, e and f are the same or different and each represents an integer of 0 to 5, with a proviso that each $R^{h1}$, $R^{h2}$, $R^{h3}$, $R^{h4}$, $R^{h5}$ and $R^{h6}$ may be different when a, b, c, d, e or f is not less than 2.

(HT 2)

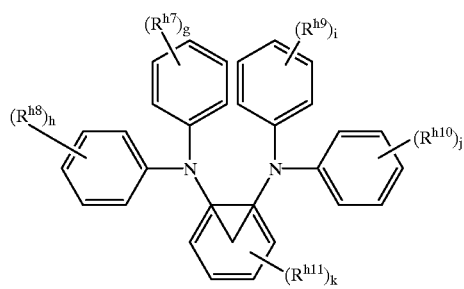

wherein $R^{h7}$, $R^{h8}$, $R^{h9}$, $R^{h10}$ and $R^{h11}$ are the same or different and each represents a halogen atom, an alkyl group which may have a substituent, an alkoxy group which may have a substituent, or an aryl group which may have a substituent, with a proviso that each $R^{h7}$, $R^{h8}$, $R^{h9}$, $R^{h10}$ and $R^{h11}$ may be different when g, h, I, j or k is not less than 2.

(HT 3)

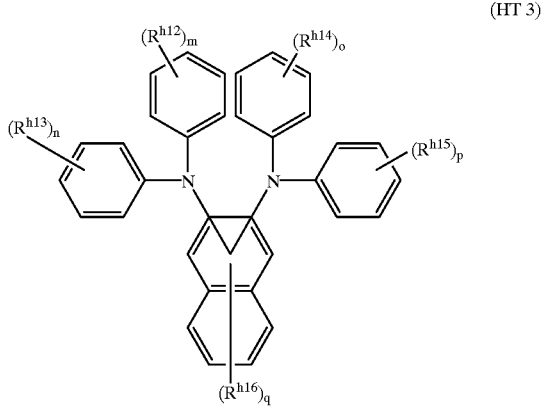

wherein $R_{h12}$, $R^{h13}$, $R^{h14}$ and $R^{h15}$ are the same or different and each represents a halogen atom, an alkyl group which may have a substituent, an alkoxy group which may have a substituent, or an aryl group which may have a substituent; and $R^{h16}$ represents a halogen atom, a cyano group, an alkyl group which may have a substituent, an alkoxy group which may have a substituent, or an aryl group which may have a substituent, with a proviso that each $R^{h12}$, $R^{h13}$, $R^{h14}$, $R^{h15}$ and $R^{h16}$ may be different when m, n, o, p or q is not less than 2.

(HT 4)

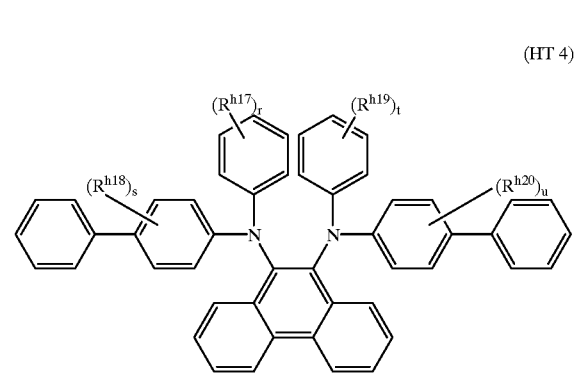

wherein $R^{h17}$, $R^{h18}$, $R^{h19}$ and $R^{h20}$ are the same or different and each represents a halogen atom, an alkyl group which may have a substituent, an alkoxy group which may have a substituent, or an aryl group which may have a substituent; and r, s, t and u are the same or different and each represents an integer of 0 to 5, with a proviso that each $R^{h17}$, $R^{h18}$, $R^{h19}$ and $R^{h20}$ may be different when r, s, t or u is not less than 2.

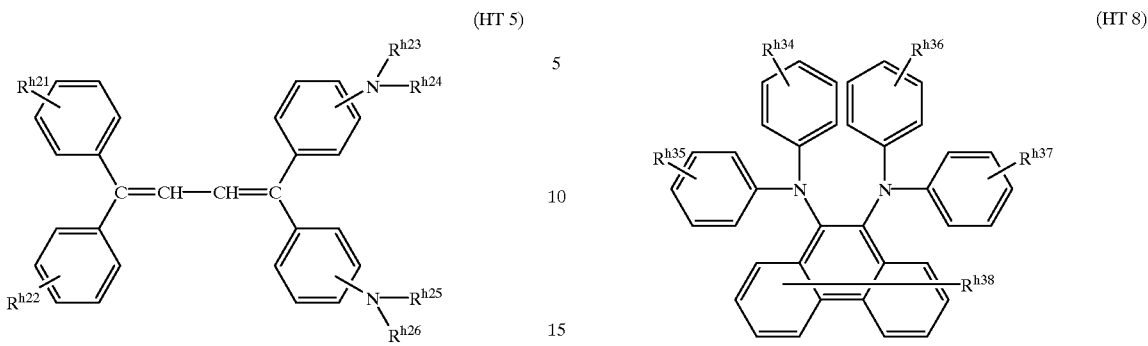

wherein $R^{h21}$, and $R^{h22}$ are the same or different and each represents a hydrogen atom, a halogen atom, an alkyl group, or an alkoxy group; and $R^{h23}$, $R^{h24}$, $R^{h25}$ and $R^{h26}$ are the same or different and each represents a hydrogen atom, an alkyl group, or an aryl group.

wherein $R^{h34}$, $R^{h35}$, $R^{h36}$, $R^{h37}$ and $R^{h38}$ are the same or different and each represents a hydrogen atom, a halogen atom, an alkyl group, or an alkoxy group.

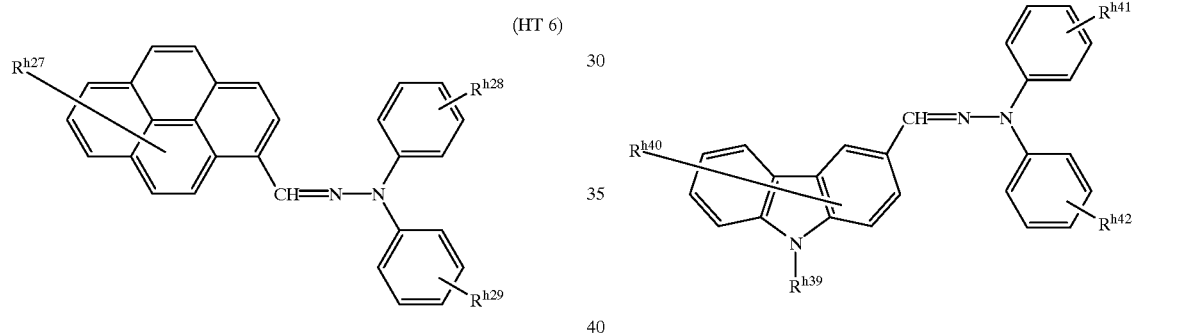

wherein $R^{h27}$, $R^{h28}$ and $R^{h29}$ are the same or different and each represents a hydrogen atom, a halogen atom, an alkyl group, or an alkoxy group.

wherein $R^{h39}$ represents a hydrogen atom or an alkyl group; and $R^{h40}$, $R^{h41}$ and $R^{h42}$ are the same or different and each represents a hydrogen atom, a halogen atom, an alkyl group, or an alkoxy group.

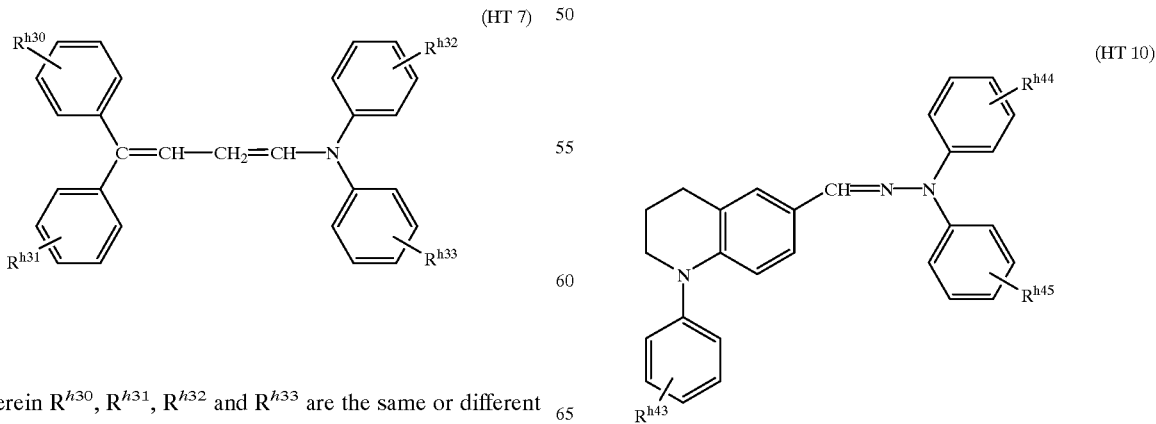

wherein $R^{h30}$, $R^{h31}$, $R^{h32}$ and $R^{h33}$ are the same or different and each represents a hydrogen atom, a halogen atom, an alkyl group, or an alkoxy group.

wherein $R^{h43}$, $R^{h44}$ and $R^{h45}$ are the same or different and each represents a hydrogen atom, a halogen atom, an alkyl group, or an alkoxy group.

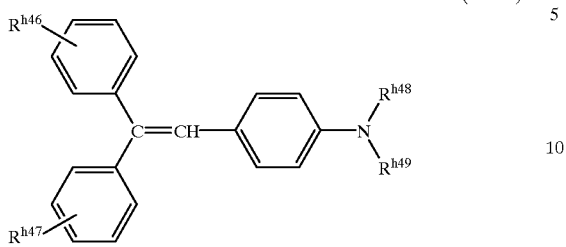
(HT 11)

wherein $R^{h46}$ and $R^{h47}$ are the same or different and each represents a hydrogen atom, a halogen atom, an alkyl group which may have a substituent, or an alkoxy group which may have a substituent; and $R^{h48}$ and $R^{h49}$ are the same or different and each represents a hydrogen atom, an alkyl group which may have a substituent, or an aryl group which may have a substituent.

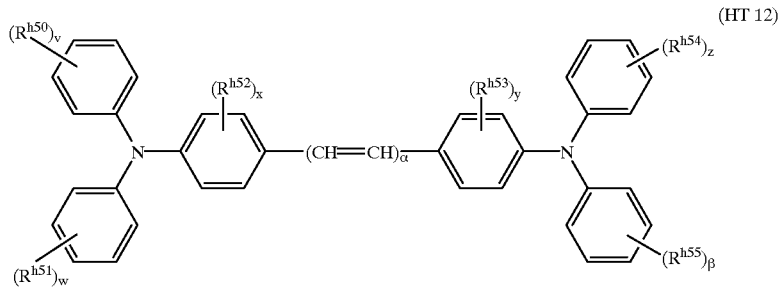
(HT 12)

wherein $R^{h50}$, $R^{h51}$, $R^{h52}$, $R^{h53}$ and $R^{h55}$ are the same or different and each represents an alkyl group which may have a substituent, an alkoxy group which may have a substituent, or an aryl group which may have a substituent; α represents an integer of 1 to 10; and v, w, x, y, z and β are the same or different and each represents an integer of 0 to 2, with a proviso that each $R^{h50}$, $R^{h51}$, $R^{h52}$, $R^{h53}$ and $R^{h55}$ may be different when v, w, x, y, z or β is 2.

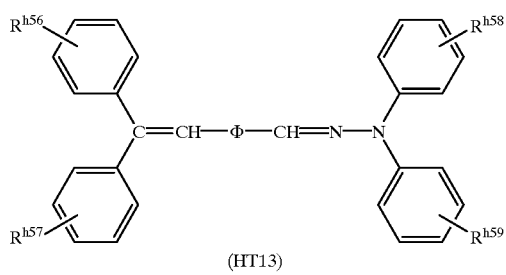
(HT13)

wherein $R^{h56}$, $R^{h57}$, $R^{h58}$, and $R^{h59}$ are the same or different and each represents a hydrogen atom, a halogen atom, an alkyl group, or an alkoxy group; and Φ represents (Φ-1), (Φ-2), or (Φ-3) represented by the following formulas:

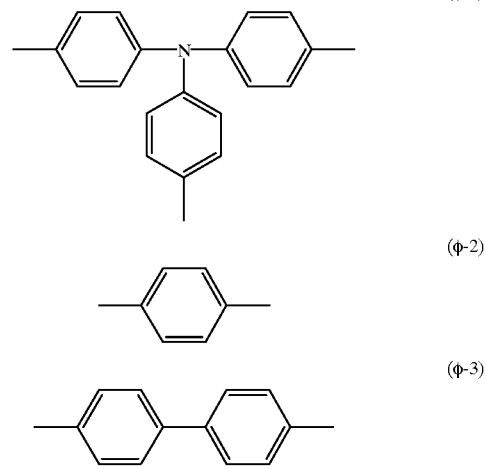

In the hole transferring materials listed above, the alkyl group, alkoxy group, aryl group, aralkyl group and halogen atom include the same groups as those described above.

The substituent with which the above groups may be substituted includes, for example, halogen atom, amino group, hydroxyl group, optionally esterified carboxyl group, cyano group, alkyl group having 1 to 6 carbon atoms, alkoxy group having 1 to 6 carbon atoms, or alkenyl group having 2 to 6 carbon atoms, which may have an aryl group. The substitution position of the substituent is not specifically limited.

In the present invention, there can also be used conventionally known hole transferring substances, i.e. nitrogen-containing cyclic compounds and condensed polycyclic compounds, for example, oxadiazole compound such as 2,5-di(4-methylaminophenyl)-1,3,4-oxadiazole, styryl compound such as 9-(4-diethylaminostyryl)anthracene, carbazole compound such as polyvinylcarbazole, organopolysilane compound, pyrazoline compound such as 1-phenyl-3-(p-dimethylaminophenyl)pyrazoline, hydrazone compound, triphenylamine compound, indole compound, oxazole compound, isoxazole compound, thiazole compound, thiadiazole compound, imidazole compound, pyrazole compound, and triazole compound, together with or in place of the hole transferring materials (HT1) to (HT13) described above.

In the present invention, these hole transferring materials can be used alone, or two or more kinds of them can be used in combination. When using the hole transferring material having film-forming properties such as polyvinylcarbazole, a binder resin is not required necessarily.

\<Electron acceptor\>

In the electrophotosensitive material of the present invention, the electron acceptor may be contained in the photosensitive layer, together with the naphthoquinone derivative (1) of the present invention.

Such an electron acceptor includes various compounds having high electron transferability, for example, compounds represented by the general formulas (ET1) to (ET17).

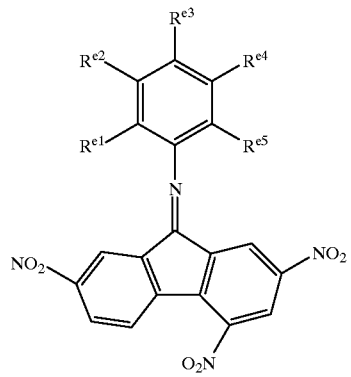

(ET 1)

wherein $R^{e1}$, $R^{e2}$, $R^{e3}$, $R^{e4}$ and $R^{e5}$ are the same or different and each represents a hydrogen atom, an alkyl group which may have a substituent, an alkoxy group which may have a substituent, an aryl group which may have a substituent, an aralkyl group which may have a substituent, a phenoxy group which may have a substituent, or a halogen atom.

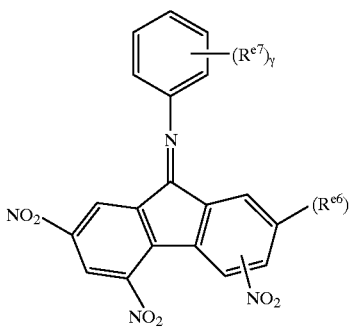

(ET 2)

wherein $R^{e6}$ represents an alkyl group; $R^{e7}$ represents an alkyl group which may have a substituent, an alkoxy group which may have a substituent, an aryl group which may have a substituent, an aralkyl group which may have a substituent, a halogen atom, or an alkyl halide group; and γ represents an integer of 0 to 5, with a proviso that each $R^{e7}$ may be different with each other when γ is not less than 2.

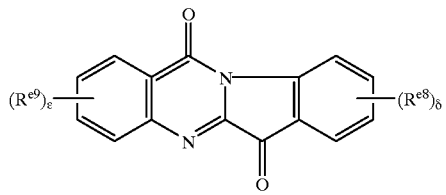

(ET 3)

wherein $R^{e8}$ and $R^{e9}$ are the same or different and each represents an alkyl group; δ represents an integer of 1 to 4; and ε represents an integer of 0 to 4, with a proviso that each $R^{e8}$ and $R^{e9}$ may be different when δ and ε are not less than 2.

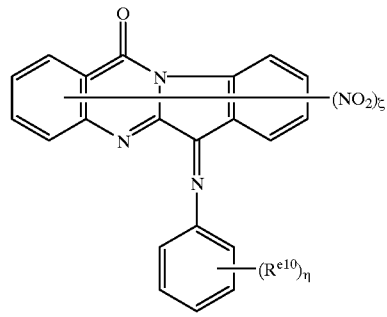

(ET 4)

wherein $R^{e10}$ represents an alkyl group, an aryl group, an aralkyl group, an alkoxy group, an alkyl halide group, or a halogen atom; ζ represents an integer of 0 to 4; and η represents an integer of 0 to 5, with a proviso that each $R^{e10}$ may be different when η is not less than 2.

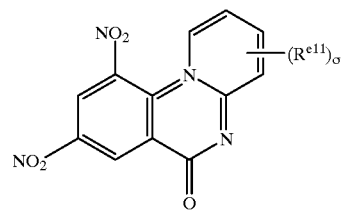

(ET 5)

wherein $R^{e11}$ represents an alkyl group, with a proviso that each $R^{e11}$ may be different when σ is not less than 2.

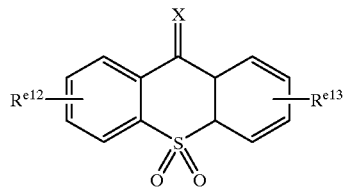

(ET 6)

wherein $R^{e12}$ and $R^{e13}$ are the same or different and each represents a hydrogen atom, a halogen atom, an alkyl group, an aryl group, an aralkyloxycarbonyl group, an alkoxy group, a hydroxyl group, a nitro group, or a cyano group; and X represents an oxygen atom, a =N—CN group, or a =C(CN)$_2$ group.

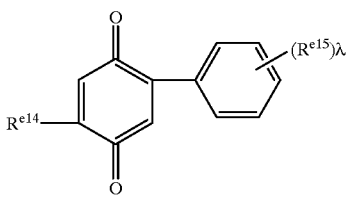

(ET 7)

wherein $R^{e14}$ represents a hydrogen atom, a halogen atom, an alkyl group, or a phenyl group which may have a substituent; $R^{e15}$ represents a halogen atom, an alkyl group which may have a substituent, or a phenyl group which may have a substituent, an alkoxycarbonyl group, a N-alkylcarbamoyl group, a cyano group, or a nitro group; and λ represents an integer of 0 to 3, with a proviso that each $R^{e15}$ may be different with each other when λ is not less than 2.

(ET 8)

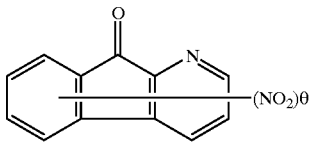

wherein θ represents an integer of 1 to 2.

(ET 9)

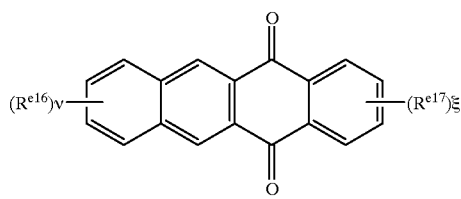

wherein $R^{e16}$ and $R^{e17}$ are the same or different and each represents a halogen atom, an alkyl group which may have a substituent, a cyano group, a nitro group, or an alkoxycarbonyl group; and ν and ξ each represents an integer of 0 t 3, with a proviso that each $R^{e16}$ and $R^{e17}$ may be different with each other when ν and ξ are not less than 2.

(ET 10)

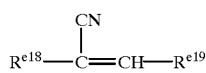

wherein $R^{e18}$ and $R^{e19}$ are the same or different and each represents a phenyl group, a condensed polycyclic group, or a heterocyclic group, with a proviso that these groups may have a substituent.

(ET 11)

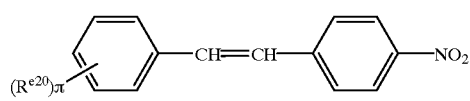

wherein $R^{e20}$ represents an amino group, a dialkylamino group, an alkoxy group, an alkyl group, or a phenyl group; and π represents an integer of 1 to 2, with a proviso that each $R^{e20}$ may be different with each other when π is 2.

(ET 12)

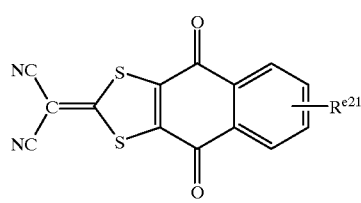

wherein $R^{e21}$ represents a hydrogen atom, an alkyl group, an aryl group, an alkoxy group, or an aralkyl group.

(ET 13)

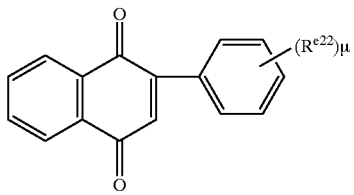

wherein $R^{e22}$ represents a halogen atom, an alkyl group which may have a substituent, a phenyl group which may have a substituent, an alkoxycarbonyl group, a N-alkylcarbamoyl group, a cyano group, or a nitro group; μ represents an integer of 0 to 3, with a proviso that each $R^{e22}$ may be different with each other when μ is not less than 2.

(ET 14)

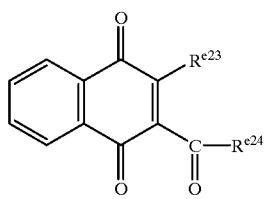

wherein $R^{e23}$ represents an alkyl group which may have a substituent or an aryl group which may have a substituent; $R^{e24}$ represents analkyl groupwhichmayhavea substituent, an aryl group which may have a substituent, or a group:

in which $R^{e24a}$ represents an alkyl group which may have a substituent or an aryl group which may have a substituent.

(ET 15)

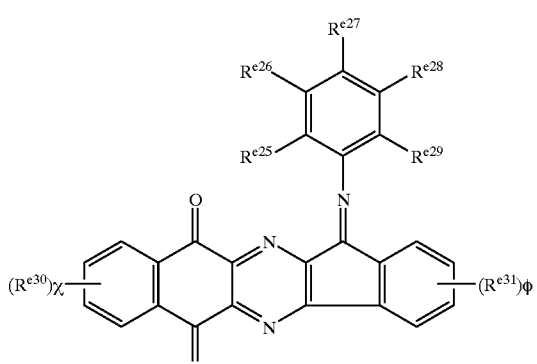

wherein $R^{e25}$, $R^{e26}$, $R^{e27}$, $R^{e28}$, $R^{e29}$, $R^{e30}$ and $R^{e31}$ are the same or different and each represents an alkyl group, an aryl group, an aralkyl group, an alkoxy group, a halogen atom, or an alkyl halide group; and x and φ are the same or different and each represents an integer of 0 to 4.

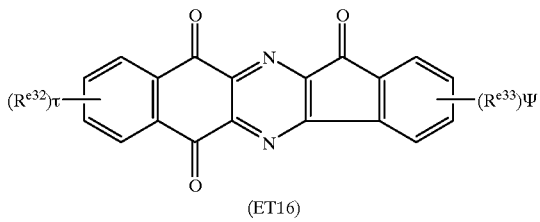

(ET16)

wherein $R^{e32}$ and $R^{e33}$ are the same or different and each represents an alkyl group, an aryl group, an alkoxy group, a halogen atom, or an alkyl halide group; and τ and ψ are the same or different and each represents an integer of 0 to 4.

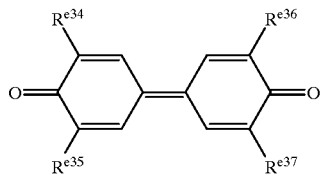

(ET 17)

wherein $R^{e34}$, $R^{e35}$, $R^{e36}$ and $R^{e37}$ are the same or different and each represents a hydrogen atom, an alkyl group, an alkoxy group, an aryl group, an aralkyl group, a cycloalkyl group, or an amino group, with a proviso that at least two substituents of $R^{e34}$, $R^{e35}$, $R^{e36}$ and $R^{e37}$ are the same groups other than a hydrogen atom.

In the electron acceptor listed above, the alkyl group, alkoxy group, aryl group, aralkyl group, cycloalkyl group, alkoxycarbonyl group, heterocyclic group and halogen atom include the same groups as those described above.

The alkyl group and halogen atom in the alkyl halide group include the same groups as those described above.

Thecondensed polycyclic group includes, for example, naphthyl, phenanthryl, or anthryl. The aralkyloxycarbonyl group includes, for example, those whose aralkyl moiety is each of various aralkyl groups described above. The N-alkylcarbamoyl group includes, for example, those whose alkyl moiety is each of various alkyl groups described above.

The dialkylamino group includes, for example, those whose alkyl moiety is each of various alkyl groups described above. Two alkyl(s) with which an amine is substituted may be the same or different.

The substituent with which the above groups may be substituted includes, for example, halogen atom, amino group, hydroxyl group, optionally esterified carboxyl group, cyano group, alkyl group having 1 to 6 carbon atoms, alkoxy group having 1 to 6 carbon atoms, or alkenyl group having 2 to 6 carbon atoms, which may have an aryl group. The substitution position of the substituent is not specifically limited.

In the present invention, there can be used conventionally known electron transferring substances, for example, benzoquinone compound (e.g., p-benzoquinone, 2,6-di-t-butylbenzoquinoe), malononitrile, thiopyran compound, tetracyanoethylenecyanethylene, 2,4,8-trinitrothoxane, dinitrobenzene, dinitroanthracene, dinitroacridine, nitroanthraquinone, dinitroanthraquinone, succinic anhydride, maleic anhydride, and dibromomaleic anhydride, in addition to those described above. In the present invention, these electron transferring materials can be used alone or two or more kinds of them can be used in combination.

<Binder resin>

As the binder resin in which the above respective components are dispersed, there can be used various resins which have hitherto been used in the photosensitive layer. For example, there can be used thermoplastic resins such as styrene polymer, styrene-butadiene copolymer, styrene-acrylonitrile copolymer, styrene-maleic acid copolymer, acrylic polymer, styrene-acrylic copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyacrylate, polusulfone, diallyl phthalate resin, ketone resin, polyvinyl butyral resin, polyether resin, and polyester resin; crosslinkable thermosetting resins such as silicone resin, epoxy resin, phenol resin, urea resin, and melamine resin; and photocurable resins such as epoxy acrylate and urethane acrylate.

In addition to the above respective components, various conventionally known additives such as antioxidants, radical scavengers, singlet quenchers, deterioration inhibitors (e.g. ultraviolet absorbers), softeners, plasticizers, surface modifiers, extenders, thickeners, dispersion stabilizers, waxes, acceptors, and donors can be incorporated into the photosensitive layer as far as these additives do not exert a deleterious influence on electrophotographic characteristics. To improve the sensitivity of the photosensitive layer, for example, known sensitizers such as terphenyl, halonaphthoquinones, and acenaphthylene may be used in combination with the electric charge generating material.

In the single-layer type photosensitive material, the electric charge generating material may be incorporated in an amount within a range from 0.1 to 50 parts by weight, and preferably from 0.5 to 30 parts by weight, based on 100 parts by weight of the binder resin. The naphthoquinone derivative (1) (electron transferring material) in the present invention may be incorporated in an amount within a range from 5 to 100 parts by weight, and preferably from 10 to 80 parts by weight, based on 100 parts by weight of the binder resin. When the electron acceptor is contained in the photosensitive layer, the amount of the electron acceptor is within a range from 0.1 to 40 parts by weight, and preferably from 0.5 to 20 parts by weight, based on 100 parts by weight of the binder resin. When the hole transferring material is contained, the amount of the hole transferring material is within a range from 5 to 500 parts by weight, and preferably from 25 to 200 parts by weight, based on 100 parts by weight of the binder resin. The thickness of the photosensitive layer in the single-layer type photosensitive material is within a range from 5 to 100 μm, and preferably from 10 to 50 μm.

In the multi-layer type photosensitive material, the electric charge generating material and binder resin, which constitute the electric charge generating layer, may be used in various proportions. The electric charge generating material is incorporated in an amount within a range from 5 to 1000 parts by weight, and preferably from 30 to 500 parts by weight, based on 100 parts by weight of the binder resin. When the hole transferring material or electron acceptor is contained in the electric charge generating layer, the amount of the hole transferring material or electron acceptor is within a range from 0.1 to 100 parts by weight, and preferably from 0.5 to 80 parts by weight, based on 100 parts by weight of the binder resin.

The electron transferring material and binder resin, which constitute the electric charge transferring layer, can be used in various proportions as far as they do not cause inhibition of transfer of electric charges and crystallization. The naphthoquinone derivative (1) (electron transferring material) in the present invention may be incorporated in an amount within a range from 10 to 500 parts by weight, and preferably from 25 to 100 parts by weight, based on 100 parts by weight of the binder resin so that electric charges generated by irradiation with light in the electric charge generating layer can be easily transferred. When the electron acceptor is contained in the electric charge transferring layer, the amount of the electron acceptor is within a range from 0.1 to 40 parts by weight, and preferably from 0.5 to 20 parts by weight, based on 100 parts by weight of the binder resin. When the hole transferring material is contained in the electric charge transferring layer, the amount of the hole transferring material is within a range from 5 to 200 parts by weight, and preferably from 10 to 80 parts by weight, based on 100 parts by weight of the binder resin.

A barrier layer may be formed between the conductive substrate and photosensitive layer in the single-layer type photosensitive material, while the barrier layer may be formed between the conductive substrate and electric charge generating layer, between the conductive substrate and electric charge transferring layer, or between the electric charge generating layer and electric charge transferring layer in the multi-layer type photosensitive material as far as it does not inhibit characteristics of the photosensitive material. A protective layer may be formed on the surface of the photosensitive material.

As the conductive substrate on which the photosensitive layer is formed, for example, various materials having the conductivity can be used. The conductive substrate includes, for example, metallic simple substances such as iron, aluminum, copper, tin, platinum, silver, vanadium, molybdenum, chrome, cadmium, titanium, nickel, palladium, indium, stainless steel, and brass; plastic materials prepared by depositing or laminating the above metal; and glasses coated with aluminum iodide, tin oxide, and indium oxide.

The conductive substrate may be in the form of a sheet or drum according to the structure of the image forming apparatus to be used. The substrate itself may have the conductivity, or the surface of the substrate may have the conductivity. The conductive substrate may be preferably those having a sufficient mechanical strength on use.

When the photosensitive layer is formed by the coating method, a dispersion is prepared by dispersing and mixing the above hole transferring material, electric charge generating material, electron acceptor and binder resin, together with a proper solvent, using a known method such as roll mill, ball mill, attritor, paint shaker, and ultrasonic dispersing equipment, and then the resulting dispersion is coated by using a known means and dried.

As the solvent for preparing the dispersion, various organic solvents can be used. The organic solvent includes, for example, alcohols such as methanol, ethanol, isopropanol, and butanol; aliphatic hydrocarbons such as n-hexane, octane, and cyclohexane; aromatic hydrocarbons such as benzene, toluene, and xylene; halogenated hydrocarbons such as dichloromethane, dichloroethane, chloroform, carbon tetrachloride, and chlorobenzene; ethers such as dimethyl ether, diethyl ether, tetrahydrofuran, ethylene glycol dimethyl ether, and diethylene glycol dimethyl ether; ketones such as acetone, methyl ethyl ketone, and cylohexanone; esters such as ethyl acetate and methyl acetate; and dimethylformaldehyde, dimethylformamide, and dimethyl sulfoxide. These solvents can be used alone, or two or more kinds of them can be used in combination.

To improve the dispersion properties of the electric charge generating material, hole transferring material and electron transferring material, and the smoothness of the surface of the photosensitive layer, for example, surfactants and leveling agents may be used.

EXAMPLES

The following Synthesis Examples, Examples and Comparative Examples further illustrate the present invention in detail.

<Synthesis of Naphthoquinone Derivative>

Reference Example 1

The compound of the above formula (4) (1.0 g, 4.7 mmol) and silver nitrate (3.8 g, 22 mmol) were added in 50 ml of ethanol and, after stirring, the mixture was refluxed for 20 minutes. After the reaction mixture was cooled, the deposited solid was removed by filtration and the filtrate was extracted with $CHCl_3$ three times. The organic layer was washed with water and dehydrated with anhydrous sodium sulfate. Then, the organic 22 solvent was distilled off to obtain a residue, which was purified by silica gel column chromatography (developing solution: chloroform-hexane) to obtain 0.98 g of the compound of the above formula (3) (yield: 83%).

Reference Example 2

After the compound (3) (4.58 g, 10 mmol) was dissolved in 100 ml of methanol and methyl iodide (3.4 g, 23 mmol) was added, $NaOCH_3$ (prepared by reacting 0.53 g of Na atoms with 70 ml of methanol) was added dropwise for 10 minutes and the mixture was stirred at room temperature for four hours. The reaction mixture was added to an aqueous hydrochloric acid solution and the mixed solution was extracted with chloroform three times. The organic layer was washed with water and dehydrated with anhydrous sodium sulfate. Then, the organic solvent was distilled off and the resulting residue was purified by silica gel column chromatography (developing solution: chloroform-hexane) to obtain 3.60 g of the above compound (2-1) (yield: 75.0%).

Reference Example 3

After the compound (3) (3.5 g, 7.6 mmol) was dissolved in 100 ml of ethanol and ethyl iodide (2.6 g, 19 mmol) was added, $NaOC_2H_5$ (prepared by reacting 0.45 g of Na atoms with 70 ml of ethanol) was added dropwise for 10 minutes and the mixture was stirred at room temperature for four hours. The reaction mixture was added to an aqueous hydrochloric acid solution and the mixed solution was extracted with chloroform three times. The organic layer was washed with water and dehydrated with sodium hydroxide. Then, the organic solvent was distilled off and the resulting residue was purified by silica gel column chromatography (developing solution: chloroform-hexane) to obtain 2.8 g of the compound (2-3) represented by the following general formula (yield: 71.6%).

(Compound 2-3)

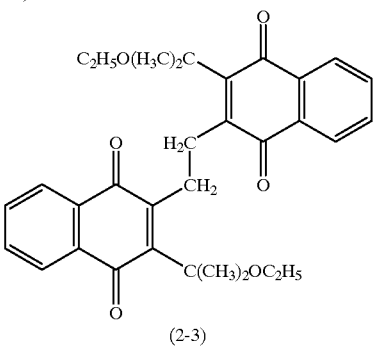

(2-3)

Synthesis Example 1

The compound (2-1) (3.2 g, 6.6 mmol) was dissolved in 30 ml of toluene and 2,3-dihydro-5,6-dicyclo-1,4-benzoquinone (DDQ) (3.7 g, 16 mmol) was added, and then the mixture was refluxed for 24 hours. After the reaction mixture was cooled and the deposited, the deposited solid was removed by filtration and the organic layer was distilled off. The residue was purified by silica gel column chromatography (developing solution: chloroform) to obtain 1.02 g of a naphthoquinone derivative corresponding to the compound (1-1) in Table 1 (yield: 32.2%, melting point: 223–225° C., elemental analysis: C,74.44; H,5.81; O,19.92).

An infrared absorption spectrum of the naphthoquinone derivative corresponding to the compound (1-1) in Table 1 is shown in FIG. 1.

Synthesis Example 2

In the same manner as in Synthesis Example 1, except that the compound (2-3) (2.0 g, 3.9 mmol) was used in place of the compound (2-1) and the amount of DDQ was changed to 2.3 g (10 mmol), 0.8 g of a naphthoquinone derivative corresponding to the compound (1-3) in Table 1 (yield: 40.1%, melting point: 214–217° C., elemental analysis: C,74.90; H,6.29; O,18.89) was obtained.

<Production of Electrophotosensitive Material>

Example 1

5 Parts by weight of x type metal-free phthalocyanine (CG-1) as the electric charge generating material, 100 parts by weight of polycarbonate as the binding resin, 800 parts by weight of tetrahydrofuran as the solvent, 50 parts by weight of N,N,N',N'-tetrakis(3-methylphenyl)-3,-3'-diaminobenzidine (a compound belonging to the general formula HT1) as the hole transferring material, and 30 parts by weight of a naphthoquinone derivative (1-1) as the electron transferring material were mixed and dispersed in a ball mill for 50 hours to prepare a coating solution for single-layer type photosensitive material. Then, a conductive substrate (alumina tube) was coated with the coating solution using a wire bar, followed by drying at 100° C. for one hour to form a photosensitive layer having a film thickness of 20 $\mu$m, thus producing a single-layer type photosensitive material.

Example 2

In the same manner as in Example 1, except that 3 parts by weight of p-benzoquinone as the electron acceptor was added to the raw materials of the coating solution for single-layer type photosensitive material, a single-layer type photosensitive material was produced.

Example 3

In the same manner as in Example 1, except that 3 parts by weight of 2,6-di-t-butylbenzoquinone as the electron acceptor was added to the raw materials of the coating solution for single-layer type photosensitive material, a single-layer type photosensitive material was produced.

Example 4

In the same manner as in Example 1, except that 3 parts by weight of 3,5-dimethyl-3',5'-di-t-butyl-4,4'-diphenoquinone (a compound belonging to ET17 )as the electron acceptor was added to the raw materials of the coating solution for single-layer type photosensitive material, a single-layer type photosensitive material was produced.

Example 5

In the same manner as in Example 1, except that 3 parts by weight of 3,3',5,5'-tetra-t-butyl-4,4'-diphenoquinone (a compound belonging to ET 17 )as the electron acceptor was added to the raw materials of the coating solution for single-layer type photosensitive material, a single-layer type photosensitive material was produced.

Example 6

In the same manner as in Example 1 , except that a naphthoguinone derivative (1-3) was used in place of the naphthoquinone derivative (1-1), a single-layer type photosensitive material was produced.

Example 7

In the same manner as in Example 2, except that a naphthoquinone derivative (1-3) was used in place of the naphthoquinone derivative (1-1), a single-layer type photosensitive material was produced.

Example 8

In the same manner as in Example 3, except that a naphthoquinone derivative (1-3) was used in place of the naphthoquinone derivative (1-1), a single-layer type photosensitive material was produced.

Example 9

In the same manner as in Example 4, except that a naphthoquinone derivative (1-3) was used in place of the naphthoquinone derivative (1-1), a single-layer type photosensitive material was produced.

Example 10

In the same manner as in Example 5, except that a naphthoquinone derivative (1-3) was used in place of the naphthoquinone derivative (1-1), a single-layer type photosensitive material was produced.

Example 11

100 Parts by weight of X type metal-free phthalocyanine (CG1) as the electric charge generating material, 100 parts by weight of polyvinyl butyral as the binding resin, and 2000 parts by weight of tetrahydrofuran as the solvent were mixed and dispersed in a ball mill for 50 hours to prepare a coating solution for electric charge generating layer. Then, an aluminum sheet was coated with the coating solution using a wire bar, followed by drying at 100° C. for one hour to form an electric charge generating layer having a film thickness of 1 μm.

Then, 100 parts by weight of a naphthoquinone derivative (1-1) as the electron transferring material and 100 parts by weight of polycarbonate as the binding resin were mixed, together with 800 parts by weight of toluene, and dispersed in a ball mill for 50 hours to prepare a coating solution for electric charge transferring layer. Then, the electric charge generating layer was coated with the coating solution using a wire bar, followed by drying at 100° C. for one hour to form an electric charge transferring layer having a film thickness of 20 μm, thus producing a multi-layer type photosensitive material.

Example 12

In the same manner as in Example 11, except that a naphthoquinone derivative (1-3) was used in place of the naphthoquinone derivative (1-1), a multi-layer type photosensitive material was produced.

Comparative Example 1

In the same manner as in Example 1, except that a compound represented by the following formula (6) was used in place of the naphthoquinone derivative (1-1) as the electron transferring material, a single-layer type photosensitive material was produced.

Compound of the formula (6):

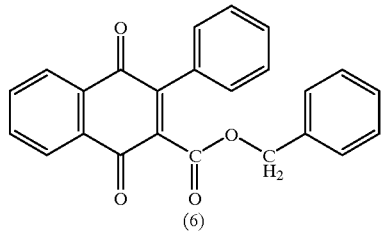

(6)

Comparative Example 2

In the same manner as in Example 2, except that the compound (6) was used in place of the naphthoquinone derivative (1-1) as the electron transferring material, a single-layer type photosensitive material was produced.

Comparative Example 3

In the same manner as in Example 3, except that the compound (6) was used in place of the naphthoquinone derivative (1-1) as the electron transferring material, a single-layer type photosensitive material was produced.

Comparative Example 4

In the same manner as in Example 4, except that the compound (6) was used in place of the naphthoquinone derivative (1-1) as the electron transferring material, a single-layer type photosensitive material was produced.

Comparative Example 5

In the same manner as in Example 5, except that the compound (6) was used in place of the naphthoquinone derivative (1-1) as the electron transferring material, a single-layer type photosensitive material was produced.

Comparative Example 6

In the same manner as in Example 1, except that a compound represented by the following formula (7) was used in place of the naphthoquinone derivative (1-1) as the electron transferring material, a single-layer type photosensitive material was produced.

Compound of formula (7):

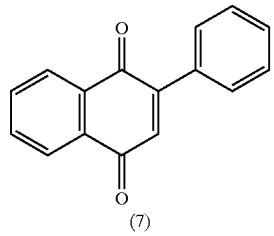

(7)

Comparative Example 7

In the same manner as in Example 2, except that the compound (7) was used in place of the naphthoquinone derivative (1-1) as the electron transferring material, a single-layer type photosensitive material was produced.

Comparative Example 8

In the same manner as in Example 3, except that the compound (7) was used in place of the naphthoquinone derivative (1-1) as the electron transferring material, a single-layer type photosensitive material was produced.

Comparative Example 9

In the same manner as in Example 4, except that the compound (7) was used in place of the naphthoquinone derivative (1-1) as the electron transferring material, a single-layer type photosensitive material was produced.

Comparative Example 10

In the same manner as in Example 5, except that the compound (7) was used in place of the naphthoquinone derivative (1-1) as the electron transferring material, a single-layer type photosensitive material was produced.

Comparative Example 11

In the same manner as in Example 11, except that the compound (6) was used in place of the naphthoquinone derivative (1-1) as the electron transferring material, a multi-layer type photosensitive material was produced.

Comparative Example 12

In the same manner as in Example 11, except that the compound (7) was used in place of the naphthoquinone derivative (1-1) as the electron transferring material, a multi-layer type photosensitive material was produced.

<Electrical Characteristics Test>

Using a drum sensitivity tester manufactured by GENETEC Co., a voltage was applied on the surface of the photosensitive materials obtained in the respective Examples and Comparative Examples to charge the surface at +700 V±20 V and the surface potential VO (V) was measured. Then, the surface of each photosensitive material (irradiation time: 80 msec.) was irradiated with monochromic light having a wavelength of 780 nm (half-width: 20 nm, light intensity: 16 μW/cm$^2$) from white light of a halogen lamp as an exposure light source through a band-pass filter, and then a surface potential at the time at which 330 seconds have passed since the beginning of exposure was measured as a residual potential Vr (V).

The kind of the electric charge generating material, hole transferring material, electron transferring material and electron acceptor used in the respective Examples and Comparative Examples as well as measurement results of the residual potential Vr are shown in Table 2 and Table 3.

The results in Table 3 exhibit that a multi-layer type photosensitive material having lower residual potential Vr also can be produced more advantageously when the naphthoquinone derivative (1-1) or (1-3) is used, as compared with use of the compound (6) or (7).

The disclosure of Japanese Patent Application Serial No. 11-184611, filed on Jun. 30, 1999, is incorporated herein by reference.

What is claimed is:

TABLE 2

|  | Type of photosensitive material | Electric charge generating material | Hole transferring material | Electron transferring material | Electron acceptor | Residual potential Vr |
| --- | --- | --- | --- | --- | --- | --- |
| Example 1 | Single-layer | CG1 | E | 1-1 | — | 165 |
| Example 2 | Single-layer | CG1 | E | 1-1 | A | 115 |
| Example 3 | Single-layer | CG1 | E | 1-1 | B | 110 |
| Example 4 | Single-layer | CG1 | E | 1-1 | C | 105 |
| Example 5 | Single-layer | CG1 | E | 1-1 | D | 105 |
| Example 6 | Single-layer | CG1 | E | 1-3 | — | 163 |
| Example 7 | Single-layer | CG1 | E | 1-3 | A | 110 |
| Example 8 | Single-layer | CG1 | E | 1-3 | B | 110 |
| Example 9 | Single-layer | CG1 | E | 1-3 | C | 103 |
| Example 10 | Single-layer | CG1 | E | 1-3 | D | 102 |
| Comp. Example 1 | Single-layer | CG1 | E | 6 | — | 170 |
| Comp. Example 2 | Single-layer | CG1 | E | 6 | A | 130 |
| Comp. Example 3 | Single-layer | CG1 | E | 6 | B | 130 |
| Comp. Example 4 | Single-layer | CG1 | E | 6 | C | 120 |
| Comp. Example 5 | Single-layer | CG1 | E | 6 | D | 120 |
| Comp. Example 6 | Single-layer | CG1 | E | 7 | — | 305 |
| Comp. Example 7 | Single-layer | CG1 | E | 7 | A | 295 |
| Comp. Example 8 | Single-layer | CG1 | E | 7 | B | 290 |
| Comp. Example 9 | Single-layer | CG1 | E | 7 | C | 290 |
| Comp. Example 10 | Single-layer | CG1 | E | 7 | D | 285 |

TABLE 3

| | Type of photosensitive material | Electric charge generating material | Electron transferring material | Electron acceptor | Residual potential Vr |
| --- | --- | --- | --- | --- | --- |
| Example 11 | Multi-layer | CG1 | 1-1 | — | 250 |
| Example 12 | Multi-layer | CG1 | 1-3 | — | 247 |
| Comp. Example 11 | Multi-layer | CG1 | 6 | — | 260 |
| Comp. Example 12 | Multi-layer | CG1 | 7 | — | 410 |

In Table 2, A denotes p-benzoquinone, B denotes 2,6-di-t-butylbenzoquinone, C denotes 3,5-dimethyl-3',5'-di-t-butyl-4,4'-diphenylquinone, D denotes 3,3',5,5'-tetra-t-butyl-4,4'-diphenoquinone, and E denotes N,N,N',N'-tetrakis(3-methylphenyl)-3,3'-diaminobenzene, respectively. Other materials were represented by the formula number or compound number.

The results in Table 2 clearly show that each single-layer type photosensitive material obtained by Examples 1 to 10, in which a naphthoquinone derivative (1-1) or (1-3) is used as the electron transferring material, exhibits lower residual potential Vr as compared with that of the corresponding Comparative Example.

1. A naphthoquinone derivative represented by the general formula (1):

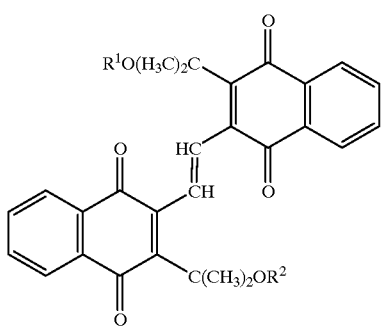

(1)

wherein R1 and R2 are the same or different and each represents a hydrogen atom or an alkyl group having 1 to 6 carbon atoms.

2. An electrophotosensitive material comprising a conductive substrate and a photosensitive layer provided on the conductive substrate, wherein the photosensitive layer contains the naphthoquinone derivative represented by the general formula (1) of claim 1.

3. The electrophotosensitive material according to claim 2, wherein an electron acceptor is contained in the photosensitive layer.

4. The electrophotosensitive material according to claim 2, wherein the photosensitive layer is a single layer.

5. The electrophotosensitive material according to claim 2, wherein the photosensitive layer contains a phthalocyanine.

6. The electrophotosensitive material according to claim 2, which is a positive charge electrophotosensitive material.

7. The electrophotosensitive material according to claim 2, wherein the photosensitive layer comprises an electric charge generating layer and an electric charge transferring layer on the upper side of the conductive substrate, wherein the electric charge generating layer is located inner side to the electric charge transferring layer.

* * * * *